(12) United States Patent
Kono et al.

(10) Patent No.: US 10,748,284 B2
(45) Date of Patent: Aug. 18, 2020

(54) IMAGE PROCESSING DEVICE, OPERATION METHOD OF IMAGE PROCESSING DEVICE, AND COMPUTER-READABLE RECORDING MEDIUM

(71) Applicant: OLYMPUS CORPORATION, Tokyo (JP)

(72) Inventors: Takashi Kono, Hachioji (JP); Yamato Kanda, Hino (JP); Takehito Hayami, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 110 days.

(21) Appl. No.: 16/193,077

(22) Filed: Nov. 16, 2018

(65) Prior Publication Data
US 2019/0089895 A1 Mar. 21, 2019

Related U.S. Application Data

(63) Continuation of application No. PCT/JP2016/065760, filed on May 27, 2016.

(51) Int. Cl.
*G06T 7/00* (2017.01)
*H04N 5/232* (2006.01)
(Continued)

(52) U.S. Cl.
CPC .......... *G06T 7/0012* (2013.01); *A61B 1/04* (2013.01); *G06T 7/246* (2017.01);
(Continued)

(58) Field of Classification Search
CPC .......... H04N 5/23229; H04N 5/23264; H04N 5/357; G06T 7/0012; G06T 7/246; G06T 2207/10068; A61B 1/04
See application file for complete search history.

(56) References Cited

U.S. PATENT DOCUMENTS 5,005,975 A * 4/1991 Kawai ................ A61B 5/0059
356/237.2
5,833,612 A * 11/1998 Eckhouse ............ A61B 5/0059
600/476
(Continued)

FOREIGN PATENT DOCUMENTS

| JP | 2005-192880 A | 7/2005 |
| JP | 2007-125373 A | 5/2007 |

(Continued)

OTHER PUBLICATIONS

International Search Report dated Aug. 23, 2016 issued in PCT/JP2016/065760.
(Continued)

*Primary Examiner* — Lin Ye
*Assistant Examiner* — Chriss S Yoder, III
(74) *Attorney, Agent, or Firm* — Scully, Scott, Murphy & Presser, P.C.

(57) ABSTRACT

An image processing device includes a processor comprising hardware, wherein the processor is configured to execute: acquiring intraluminal images; generating, for each of the intraluminal images, lesion information by estimating a visual point with respect to a lesion region extracted from each of the intraluminal images and analyzing a three-dimensional structure of the lesion, the lesion information indicating any of a top portion, a rising portion, and a marginal protruding portion in the lesion region; and extracting, based on the lesion information, a target image satisfying a prescribed condition from the intraluminal images.

25 Claims, 11 Drawing Sheets

(51) Int. Cl.
*A61B 1/04* (2006.01)
*G06T 7/246* (2017.01)
*H04N 5/357* (2011.01)

(52) U.S. Cl.
CPC ..... *H04N 5/23229* (2013.01); *H04N 5/23264* (2013.01); *H04N 5/357* (2013.01); *G06T 2207/10068* (2013.01)

(56) References Cited

U.S. PATENT DOCUMENTS

| | | | |
|---|---|---|---|
| 6,277,067 B1* | 8/2001 | Blair | A61B 1/00041 348/77 |
| 8,238,629 B2 | 8/2012 | Tanaka et al. | |
| 2007/0078335 A1* | 4/2007 | Horn | A61B 1/041 600/425 |
| 2009/0046905 A1* | 2/2009 | Lange | G06T 7/30 382/128 |
| 2014/0303435 A1 | 10/2014 | Taniguchi | |
| 2017/0004625 A1 | 1/2017 | Kamiyama et al. | |

FOREIGN PATENT DOCUMENTS

| | | |
|---|---|---|
| JP | 2007-244518 A | 9/2007 |
| JP | 2010-240000 A | 10/2010 |
| JP | 2010-287948 A | 12/2010 |
| JP | 5568196 B1 | 8/2014 |
| JP | 2015-181594 A | 10/2015 |

OTHER PUBLICATIONS

Felzenszwalb, Pedro, et al., "A Discriminatively Trained, Multiscale, Deformable Part Model", University of Chicago, pp. 1-8.

Bengio, Yoshua, "Learning deep architectures for AI", Technical Report 1312, Dept. IRO, Universite de Montreal, pp. 1-56.

Watanabe, Tomoki, "Co-occurrence Histograms of Oriented Gradients for Human Detection", IPSJ Transactions on Computer Vision and Applications, Toshiba Corporation (Mar. 2010), vol. 2, pp. 39-47.

* cited by examiner

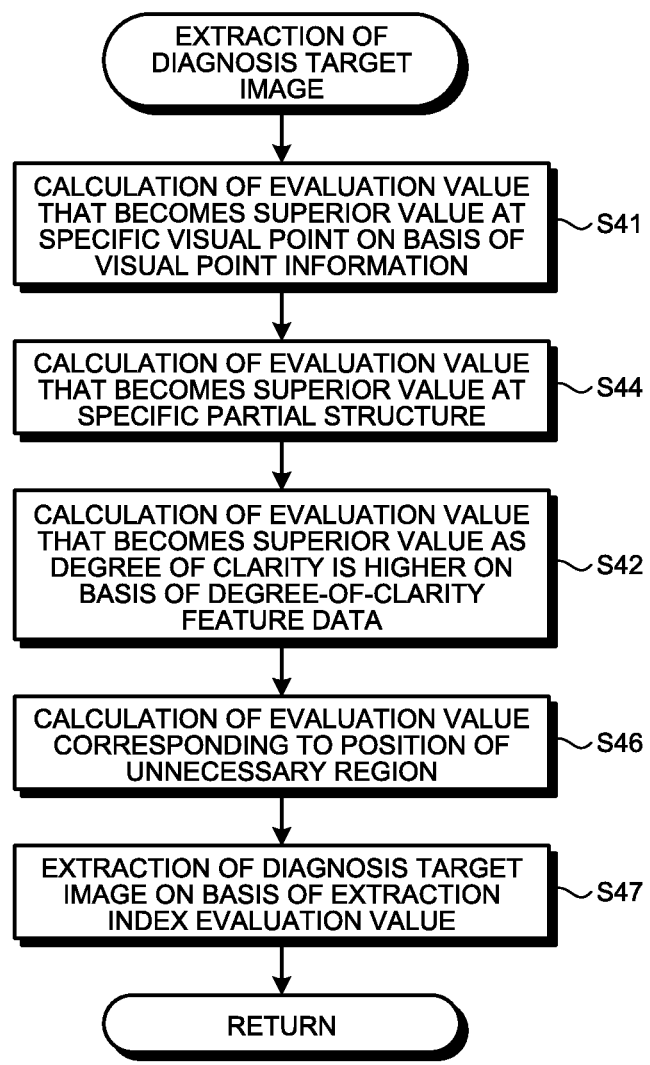

IMAGE PROCESSING DEVICE, OPERATION METHOD OF IMAGE PROCESSING DEVICE, AND COMPUTER-READABLE RECORDING MEDIUM

CROSS-REFERENCE TO RELATED APPLICATION

This application is a continuation of PCT International Application No. PCT/JP2016/065760 filed on May 27, 2016, the entire contents of which are incorporated herein by reference.

BACKGROUND

The present disclosure relates to an image processing device, an operation method of an image processing device, and a computer-readable recording medium.

As to an endoscopic diagnosis support device, there is known a technology in which image quality of an intraluminal image is evaluated by using a color drift, blur due to fluctuation or defocus, and the like, and an intraluminal image with the best image quality is extracted to appropriately diagnoses a histologically important attention region in diagnosis of a lesion. For example, in JP 2010-287948 A, first, as an image evaluation value, a total score is calculated from the degree of blur obtained from the entirety of an image, feature data indicating an average and dispersion of a color, a luminance distribution obtained from an attention region of the image, and feature data indicating complexity of an edge. Next, an endoscopic image with the best image evaluation value is extracted.

SUMMARY

According to one aspect of the present disclosure, there is provided an image processing device including a processor comprising hardware, wherein the processor is configured to execute: acquiring intraluminal images; generating, for each of the intraluminal images, lesion information by estimating a visual point with respect to a lesion region extracted from each of the intraluminal images and analyzing a three-dimensional structure of the lesion, the lesion information indicating any of a top portion, a rising portion, and a marginal protruding portion in the lesion region; and extracting, based on the lesion information, a target image satisfying a prescribed condition from the intraluminal images.

The above and other features, advantages and technical and industrial significance of this disclosure will be better understood by reading the following detailed description of the presently preferred embodiment of the disclosure, when considered in connection with the accompanying drawings.

BRIEF DESCRIPTION OF THE DRAWINGS

FIG. 14 is a flowchart illustrating diagnosis target image extraction processing that is executed by the diagnosis target image extraction unit.

DETAILED DESCRIPTION

In embodiments, image processing devices which extract an intraluminal image that is optimal for diagnosis from an intraluminal image group that is captured by an endoscope are illustrated. The intraluminal image is a color image having pixel levels (pixel values) with respect to respective color components of red (R), green (G), and blue (B) in respective pixel positions.

First Embodiment

Figure 1:
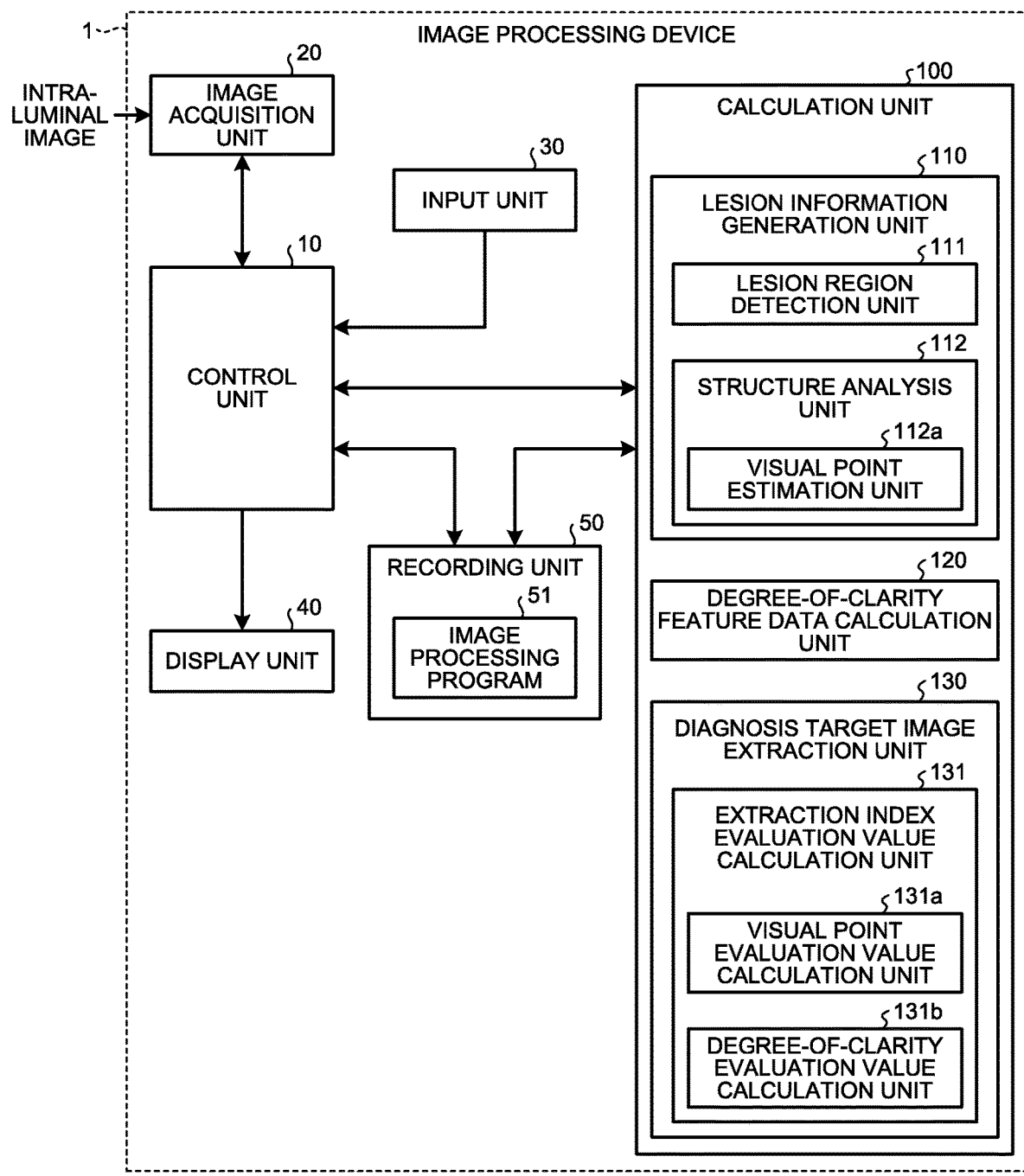
FIG. 1 is a block diagram illustrating a functional configuration of an image processing device according to a first embodiment.

FIG. 1 is a block diagram illustrating a functional configuration of an image processing device according to a first embodiment. An image processing device 1 according to the first embodiment extracts an intraluminal image that is optimal for diagnosis based on an intraluminal image group, and a lesion region that is suspected as a tumor lesion.

The image processing device 1 includes a control unit 10 that controls an operation of the entirety of the image processing device 1, an image acquisition unit 20 that acquires an intraluminal image group that is generated by capturing the inside of a lumen with an imaging device, an input unit 30 that inputs a signal corresponding to an operation from the outside to the control unit 10, a display unit 40 that performs display of various pieces of information and images, a recording unit 50 that stores image data acquired by the image acquisition unit 20 and various programs, and a calculation unit 100 that executes predetermined image processing with respect to the image data.

The control unit 10 is realized by hardware such as a central processing unit (CPU), and scans various programs recorded in the recording unit 50 to perform instruction, data transmission, and the like to respective units which constitute the image processing device 1 in accordance with an intraluminal image group input from the image acquisition unit 20, a signal input from the input unit 30, and the like, and collectively controls the operation of the entirety of the image processing device 1.

The image acquisition unit 20 is appropriately constituted in correspondence with an aspect of a system including a medical imaging device. For example, in a case of connecting the imaging device to the image processing device 1, the image acquisition unit 20 is constituted by an interface that receives an intraluminal image group that is generated in the imaging device. In addition, in a case of providing a server that retains the intraluminal image group generated by the imaging device, the image acquisition unit 20 is constituted by a communication device that is connected to the server, and the like, and acquires the intraluminal image group by performing data communication with the server. Alternatively, the intraluminal image group generated by the imaging device may be delivered by using a portable recording medium, and in this case, the image acquisition unit 20 is constituted by a reader device on which the portable recording medium is detachably mounted and which reads out the intraluminal image group of the recorded image.

For example, the input unit 30 is realized by an input device such as a keyboard, a mouse, a touch panel, and various switches, and outputs an input signal, which is generated in correspondence with an operation from the outside with respect to the input devices, to the control unit 10.

The display unit 40 is realized by a display device such as a liquid crystal display (LCD) and an electroluminescence (EL) display, and displays various screens including the intraluminal image group under control of the control unit 10.

The recording unit 50 is realized by an information recording device such as various IC memories including a ROM such as flash memory capable of performing update recording and a RAM, a hard disk that is built-in or connected with data communication terminals, and a CD-ROM, a reading device thereof, and the like. The recording unit 50 stores a program that operates the image processing device 1 and causes the image processing device 1 to execute various functions, data that is used during execution of the program, and the like in addition to the intraluminal image group that is acquired by the image acquisition unit 20. Specifically, the recording unit 50 stores an image processing program 51 that acquires lesion region information from the intraluminal image group, and extracts an intraluminal image that is optimal for diagnosis based on the lesion region information, a threshold value that can be used in the image processing, and the like.

The calculation unit 100 is realized by hardware such as a CPU, and scans the image processing program 51 to execute image processing of extracting a diagnosis target intraluminal image from the intraluminal image group.

The calculation unit 100 includes a lesion information generation unit 110, a degree-of-clarity feature data calculation unit 120, and a diagnosis target image extraction unit 130.

The lesion information generation unit 110 includes a lesion region detection unit 111 that detects a lesion region in an intraluminal image, and a structure analysis unit 112 that analyzes a structure of the lesion region. In addition, the structure analysis unit 112 includes a visual point estimation unit 112a that generates visual point information for estimating a visual point with respect to the lesion region as an index indicating a partial structure of the lesion region.

The diagnosis target image extraction unit 130 calculates an extraction index evaluation value that is an evaluation value of an extraction index, and makes a determination by using the extraction index evaluation value that is calculated, and a threshold value that is set in advance to extract an intraluminal image (hereinafter, also referred to as "diagnosis target image") that becomes a diagnosis target from a plurality of intraluminal images. The diagnosis target image extraction unit 130 includes an extraction index evaluation value calculation unit 131 that calculates the extraction index evaluation value based on the visual point information and the degree-of-clarity feature data. In addition, the extraction index evaluation value calculation unit 131 includes a visual point evaluation value calculation unit 131a that calculates an evaluation value that takes a superior value at a specific visual point as the extraction index evaluation value, and a degree-of-clarity evaluation value calculation unit 131b that calculates an evaluation value, which takes a superior value as the degree of clarity is higher, from the degree-of-clarity feature data as the extraction index evaluation value.

Figure 2:
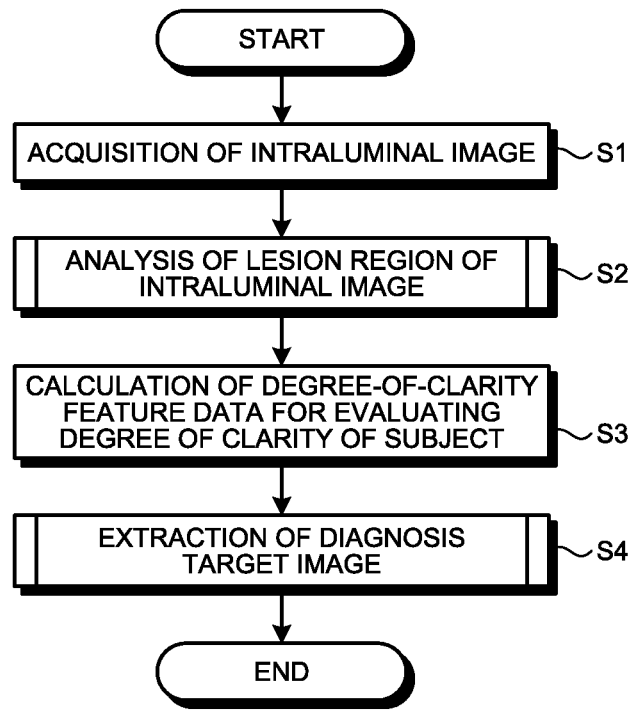
FIG. 2 is a flowchart illustrating image processing that is performed by the image processing device according to the first embodiment.

Next, an operation of the image processing device 1 will be described. FIG. 2 is a flowchart illustrating image processing that is performed by the image processing device according to the first embodiment. First, in Step S1, the image processing device 1 acquires an intraluminal image through the image acquisition unit 20. In the first embodiment, an intraluminal image, which is generated by performing image capturing by irradiating the inside of a lumen with illumination light (white light) including respective wavelength components of R, G, and B by using an endoscope, and has pixel values (an R value, a G value, and a B value) corresponding to the wavelength components at respective pixel positions, is acquired. Furthermore, the illumination light is not limited to the white light, and may be special light that includes narrow-band wavelength components of G and B, or may be illumination light that includes at least one narrow-band light of R, G, and B. For example, an intraluminal image, which is generated by performing image capturing by irradiating the inside of a lumen with special light including narrow-band wavelength components of G and B, and has pixel values (a G value and a B value) corresponding to the wavelength components at respective pixel positions, may be acquired.

Figure 3:
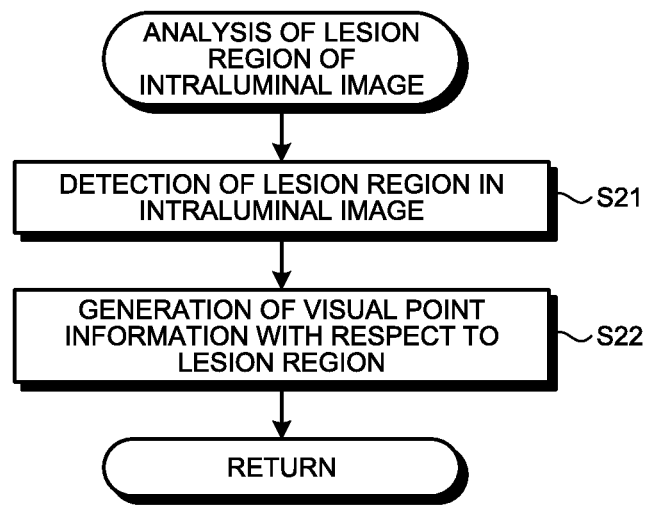
FIG. 3 is a flowchart illustrating a lesion region analysis processing that is executed by a lesion information generation unit.

In subsequent Step S2, the calculation unit 100 receives the intraluminal image and analyzes a lesion region based on the intraluminal image. FIG. 3 is a flowchart illustrating lesion region analysis processing that is executed by the lesion information generation unit 110.

In Step S21, the lesion region detection unit 111 detects a lesion region in the intraluminal image. The lesion region detection unit 111 detects the lesion region by using shape-like feature data (hereinafter, also referred to as "shape feature data").

Figure 4:
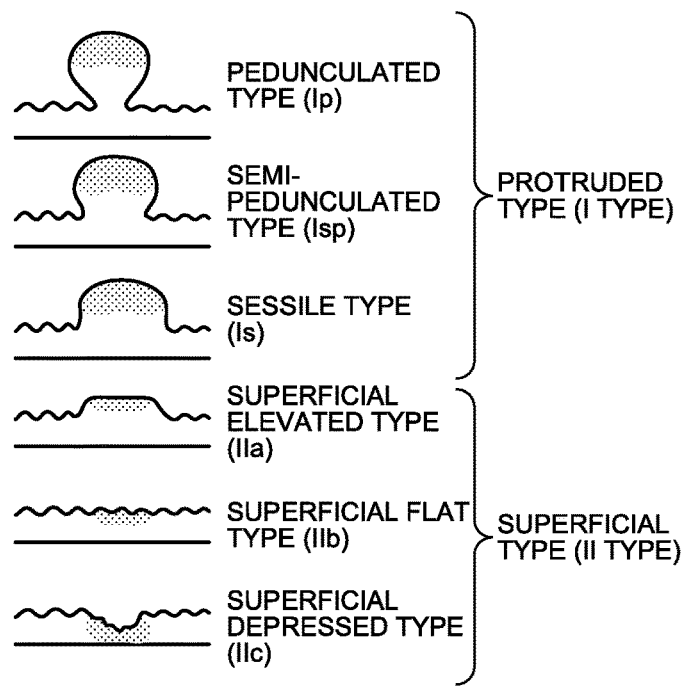
FIG. 4 is a view illustrating a specific shape of a tissue mass.

Here, the lesion region represents a region of a polyp and a tumor. Typically, the polyp is a protruding tissue mass having a diameter up to approximately 2 cm. Typically, the tumor is a protruding tissue mass having a diameter of several cm or greater. FIG. 4 is a view illustrating a characteristic shape of the tissue mass. Examples of the shape characteristic of the tissue mass include a protruded type (I type) and a superficial type (II type). In addition, examples of the protruded type (I type) include a pedunculated type (Ip) with a stem, a semi-pedunculated type (Isp) with constricted rising, and a sessile type (Is) with no constricted rising. In addition, examples of the superficial type (II type) include a superficial elevated type (IIa) in which a surface elevates, a superficial flat type (IIb) in which a surface has the same height as the periphery, and a superficial depressed type (IIc) in which a surface is depressed. In the first embodiment, it is assumed that the lesion region detection unit 111 detects a region including a tissue mass as a lesion region by using shape feature data. The reason why feature data other than the shape feature data is not used is because in feature data other than the shape feature data, for example, in texture feature data, it is likely to fail in detection of a lesion region with respect to an unclear intraluminal image. Furthermore, with regard to a specific example of lesion detection processing that uses the shape feature data, as described in JP 2007-244518 A, an edge in the intraluminal image is detected, and a lesion region is detected by analyzing feature data such as validity in an arc direction, curvature, and complexity of the edge in a tubular structure by the large intestine. In addition, it is also possible to use machine learning by a deformable parts model ((DPM), citation literature: "A Discriminatively Trained, Multiscale, Deformable Part Model", Pedro Felzenszwalb, University of Chicago) that uses the shape feature data, Deep Learning (citation literature: "Learning deep architectures for AI", Y. Bengio) that can detect a region without performing design of the feature data, and the like.

In subsequent Step S22, the visual point estimation unit 112*a* generates visual point information for estimating a visual point with respect to the lesion region as an index indicating a partial structure of the lesion region. The visual point information is information that is composed of a visual point determination value for determining at least one of an upward visual point at which surface properties in the vicinity of a top portion of a lesion are widely photographed, a lateral visual point at which surface properties of a rising portion of the lesion are widely photographed, and an inclined upward visual point at which it is easy to confirm a protruded state in the vicinity of the top portion of the lesion, and is lesion information related to a tissue mass in the intraluminal image. With the visual point information, it is possible to select an intraluminal image that is suitable for diagnosis.

Here, an example of a visual point estimation method by the visual point estimation unit 112*a* will be described below. Furthermore, the following methods are illustrative only, and there is no limitation to the following methods.
Method 1:
  1-a: An aspect ratio (=a minor axis length/a length of a major axis) of a rectangular region that is circumscribed around a lesion region is calculated.
  1-b: It is regarded that the circumscribed rectangular region becomes close to a square in a case where a circular structure is viewed from an upper side, and the value of the aspect ratio is set as upward visual point determination value. The upward visual point determination value is 0.0 to 1.0. As the upward visual point determination value approaches 1, determination can be made as the upward visual point.
Method 2:
  2-a: A contour edge intensity of the lesion region is extracted.
  2-b: First, with regard to the contour edge intensity, a section with high contour edge intensity and a section with low contour edge intensity are determined based on a threshold value that is set in advance. Continuously, a section in which the section with high contour edge intensity and the section with low contour edge intensity are successive by a predetermined number of pixels or greater is determined. Continuously, with regard to the successive section, (1-[a length of the section with low contour edge intensity])/[a length of the section with high contour edge intensity] is calculated. The calculated value becomes the lateral visual point determination value.
Method 3:
  3-a: A region, which is spaced away from a contour of the lesion region toward an outer side by a distance that is set in advance, is set as a peripheral region.
  3-b: A dispersion value of a luminance value in the peripheral region is calculated. With regard to the dispersion value, a case where the dispersion value is 0 is normalized as "1", and the maximum value of the dispersion value is normalized as "0". A value after the normalization is set as the lateral visual point determination value for determining the lateral visual point.
Method 4:
  4-a: A region, which is spaced away from a contour of the lesion region toward an outer side by a distance that is set in advance, is set as a peripheral region.
  4-b: A direction dispersion value in a gradient vector direction of luminance in the peripheral region is calculated. With regard to the direction dispersion value, a case where the direction dispersion value is 0 is normalized as "0", and the maximum value of the direction dispersion value is normalized as "1". A value after the normalization becomes the inclined upward visual point determination value for determining the inclined upward visual point. In a case where the gradient vector direction is constant, determination can be made as the inclined upward visual point. Accordingly, as the inclined upward visual point determination value approaches 0, determination can be made as the inclined upward visual point.
Method 5:
  5-a: Visual point determination values are respectively calculated by a plurality of methods including Method 1 to Method 4, and visual point information is generated by weighting all of the determination values.

The visual point estimation unit 112*a* calculates at least one determination value among the determination values for determining the upward visual point, the lateral visual point, and the inclined upward visual point, the calculated determination value is set as the visual point information. Furthermore, the determination value includes a determination value for determining a specific visual point that is set. Then, the operation of the calculation unit 100 returns to a main routine.

In Step S3 subsequent to Step S2, the degree-of-clarity feature data calculation unit 120 calculates the degree of clarity of a subject as degree-of-clarity feature data with respect to each of a plurality regions set in the intraluminal image. The degree-of-clarity feature data calculation unit 120 calculates the degree-of-clarity feature data including a combination of any one or more among a color drift amount, the degree of blur, a noise amount, a luminance-saturated area ratio, contrast information, frequency information, and edge information, or respective values thereof. With regard to the degree-of-clarity feature data according to the first embodiment, the smaller a numerical value is, the higher the degree of clarity of an image becomes. Hereinafter, an example of a method of acquiring the degree-of-clarity feature data will be described, but a calculation method is not limited thereto.

For example, the color drift amount is obtained by calculating a color average value of the intraluminal image. The noise amount is obtained as follows. A standard deviation is obtained with respect to a difference between an original image before passing through a melian filter and an image after passage, and the number of peripheral pixels which deviate from a value that is set in correspondence with the standard deviation is calculated to obtain the noise amount.

In addition, the luminance-saturated area ratio is set as a division value obtained by dividing regions in which a red color component is equal to or greater than a predetermined value by an area of an attention region. In addition, the degree of blur is obtained by calculating an average value of a range of a specific frequency component, for example, a frequency component taken by a blood vessel.

Figure 5:
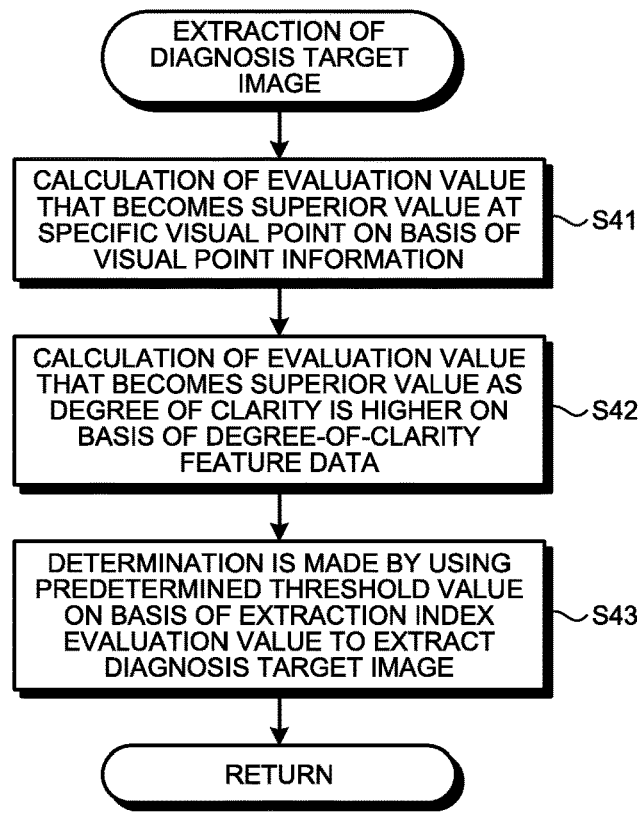
FIG. 5 is a flowchart illustrating diagnosis target image extraction processing that is executed by a diagnosis target image extraction unit.

In Step S4 subsequent to Step S3, the diagnosis target image extraction unit 130 makes a determination by using the extraction index evaluation value and a threshold value that is set in advance to extract a diagnosis target image from a plurality of the intraluminal images. FIG. 5 is a flowchart illustrating diagnosis target image extraction processing that is executed by the diagnosis target image extraction unit 130.

In Step S41, the visual point evaluation value calculation unit 131a calculates an evaluation value that takes a superior value at a specific visual point with respect to the determination value obtained in Step S2, and sets the evaluation value as an extraction index evaluation value. Here, the specific visual point represents, for example, at least one visual point in which attention needs to be paid to a lesion among the upward visual point, the lateral visual point, and the inclined upward visual point which are set by a user through the input unit 30.

The visual point evaluation value calculation unit 131a extracts an intraluminal image in which a determination value corresponding a specific visual point is the highest, and sets the determination value of the intraluminal image as an evaluation value that takes a superior value at a specific visual point. Here, respective determination values for determining the upward visual point, the lateral visual point, and the inclined upward visual point are in a range of 0.0 to 1.0, and can be determined to be more similar to the visual point as the determination values approach 1. In addition, it is assumed that the specific visual point is any one suitable for diagnosis among at least the upward visual point, the lateral visual point, and the inclined upward visual point, or a combination of two or more visual points. In a case where a plurality of determination values exists, with regard to the evaluation value that is calculated by the visual point evaluation value calculation unit 131a, the maximum value among one or more visual determination values suitable for diagnosis object is applied. Furthermore, in a case where a plurality of specific visual points are set, one evaluation value may be calculated by adding evaluation values at respective visual points, or the respective evaluation values may be respectively calculated as the visual point evaluation value.

In Step S42, the degree-of-clarity evaluation value calculation unit 131b calculates an evaluation value that takes a superior value as the degree of clarity is higher with respect to the evaluation value that is obtained in Step S3, and sets the evaluation value as the extraction index evaluation value. The degree-of-clarity evaluation value calculation unit 131b calculates the evaluation value by using a sigmoid function.

Figure 6:
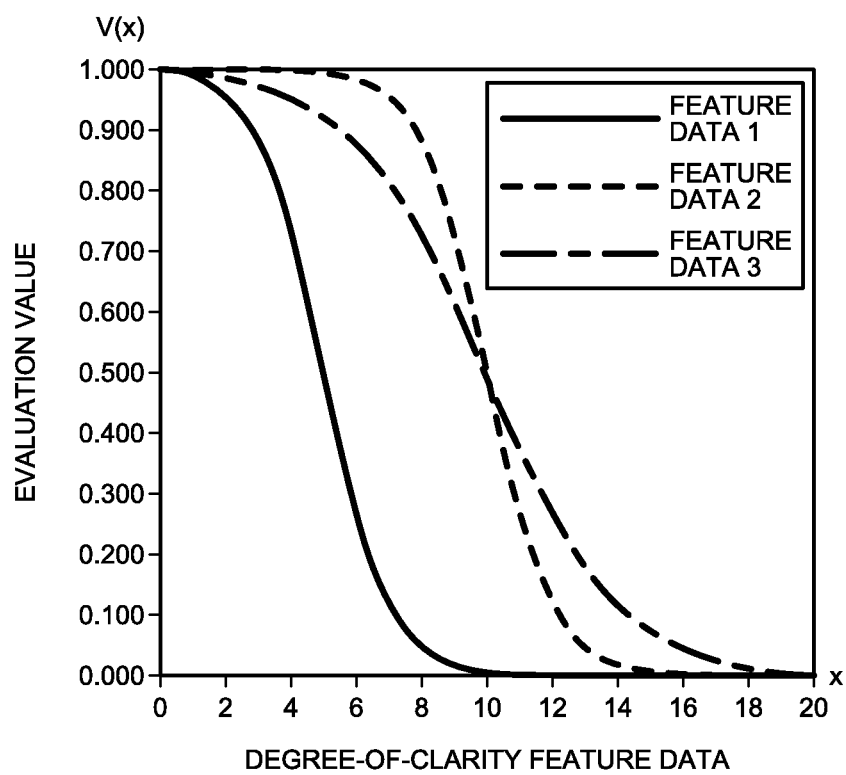
FIG. 6 is a view illustrating a sigmoid function indicating a correspondence relationship between degree-of-clarity feature data and an evaluation value.

With regard to a value of the degree-of-clarity feature data, a value that differs depending on a calculation method of the degree-of-clarity feature data calculation unit 120. Accordingly, the evaluation value that is calculated by the degree-of-clarity evaluation value calculation unit 131b is subjected to non-linear conversion by the sigmoid function prepared in correspondence with the degree-of-clarity feature data that is input, and then a value of 0.0 to 1.0 is acquired. FIG. 6 is a view illustrating the sigmoid function that indicates a correspondence relationship between the degree-of-clarity feature data and the evaluation value. The sigmoid function is a graph that is generated based on the following Expression (1) as illustrated in FIG. 6, and an evaluation value curve is generated in correspondence with a plurality of pieces of degree-of-clarity feature data (for example, feature data 1, feature data 2, and feature data 3 illustrated in FIG. 6) which are different from each other. An evaluation value (V(x)) is calculated by inputting the degree-of-clarity feature data (x). With regard to the degree-of-clarity feature data illustrated in FIG. 6, the smaller a numerical value is, the greater the degree of clarity of an image is. Furthermore, in a case where a plurality of pieces of the degree-of-clarity feature data are calculated, the degree-of-clarity evaluation value calculation unit 131b calculates an evaluation value corresponding to each piece of degree-of-clarity feature data.

$$V(x) = \frac{1}{1 + \exp(ax - b)} \quad (1)$$

In Step S43, the diagnosis target image extraction unit 130 makes a determination by using the evaluation values calculated in Steps S41 and S42, and a threshold value that is set in advance to extract a diagnosis target image. The diagnosis target image extraction unit 130 extracts an intraluminal image in which each of the evaluation value related to the visual point and the evaluation value related to the degree of clarity exceeds a threshold value that is set with respect to each of the evaluation values as the diagnosis target image.

For example, in a case where a plurality of evaluation values including the evaluation value related to the visual point and the evaluation value related to the degree of clarity are provided, the diagnosis target image extraction unit 130 determines the plurality of evaluation values step by step by using the threshold value that is set for each evaluation value to extract the diagnosis target image. In addition, an evaluation value that is close to a predetermined point in a multi-dimensional evaluation value space formed by a plurality of evaluation values may be extracted, a rank may be given to a plurality of intraluminal images having evaluation values included in a specific range based on a distance from the predetermined point, and a predetermined number of higher diagnosis target images may be extracted. When being constructed by the multi-dimensional space based on the plurality of evaluation values, a distribution of an arbitrary range may be determined to extract the diagnosis target image.

Then, the calculation unit 100 outputs the extraction result in Step S4. In correspondence with this, the control unit 10 causes the display unit 40 to display the intraluminal image that is extracted with respect to a specific visual point. In addition, the extraction result in Step S4 may be recorded in the recording unit 50. Then, the operation of the image processing device 1 is terminated.

As described above, according to the first embodiment, since the diagnosis target image is extracted based on the visual point information indicating a visual point with respect to a lesion in the intraluminal image, and the degree-of-clarity feature data that is calculated from the intraluminal image, it is possible to extract the diagnosis target image that is used in diagnosis and is suitable for the diagnosis. According to this, it is possible to extract an intraluminal image that is suitable for rear-stage processing or an object of observation.

Second Embodiment

Figure 7:
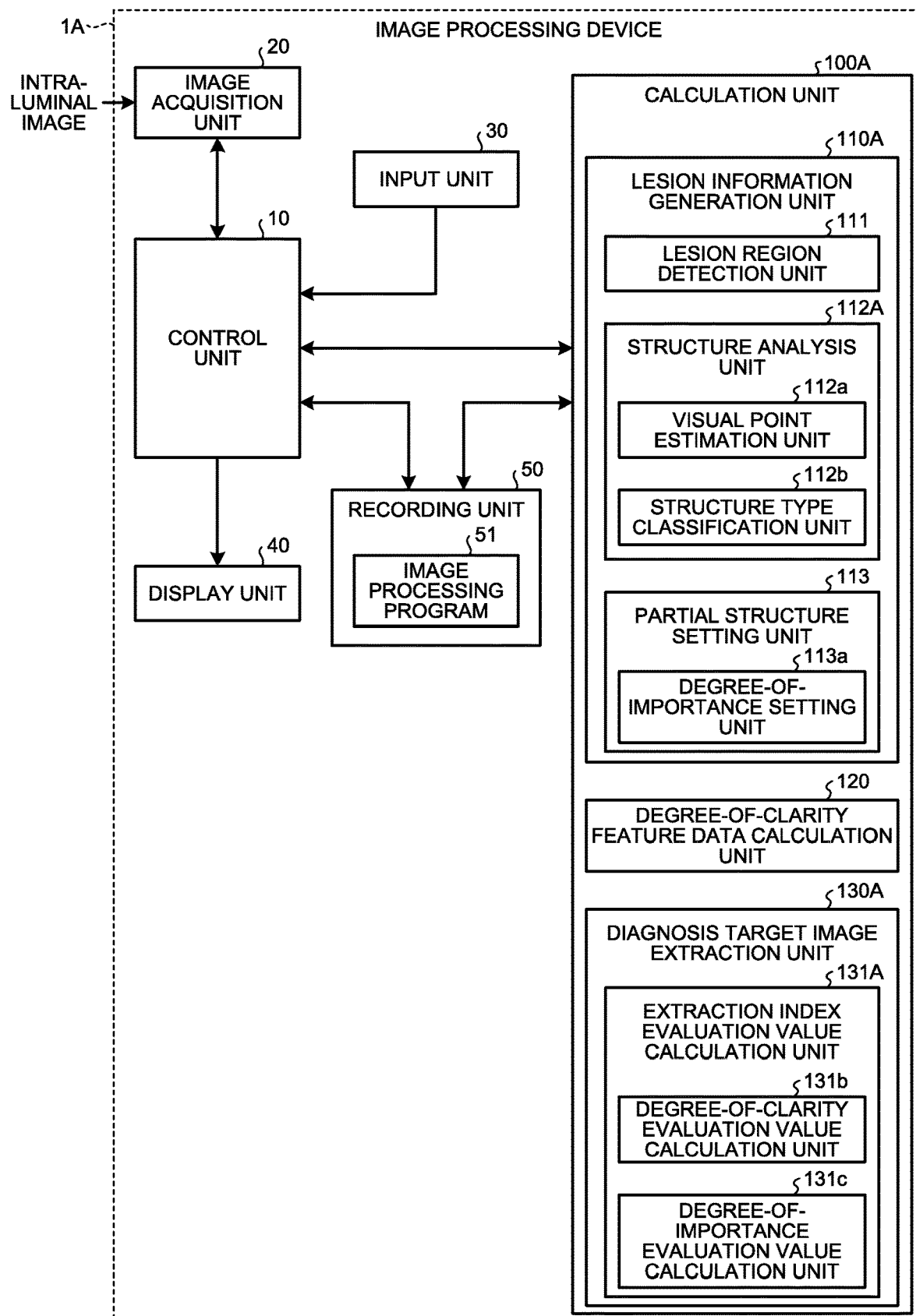
FIG. 7 is a block diagram illustrating a functional configuration of an image processing device according to a second embodiment.

FIG. 7 is a block diagram illustrating a functional configuration of an image processing device according to a second embodiment. In the following description, the same reference numerals will be given the same constituent elements as the constituent elements of the image processing device 1 according to the first embodiment. An image processing device 1A illustrated in FIG. 7 includes a control unit 10 that controls an operation of the entirety of the image processing device 1A, an image acquisition unit 20 that acquires image data that is generated by capturing the inside of a lumen with an imaging device, an input unit 30 that inputs a signal corresponding to an operation from the outside to the control unit 10, a display unit 40 that performs display of various pieces of information and images, a recording unit 50 that stores image data acquired by the image acquisition unit 20 and various programs, and a calculation unit 100A that executes predetermined image processing with respect to the image data.

The calculation unit 100A includes a lesion information generation unit 110A, a degree-of-clarity feature data calculation unit 120, and a diagnosis target image extraction unit 130A.

The lesion information generation unit 110A includes a lesion region detection unit 111 that detects a lesion region in an intraluminal image, a structure analysis unit 112A that analyzes a structure of the lesion region, and a partial structure setting unit 113 that sets a region of a specific partial structure based on the structure of the lesion region. In addition, the structure analysis unit 112A includes a visual point estimation unit 112a that generates visual point information for estimating a visual point with respect to the lesion region, and a structure type classification unit 112b that classifies the lesion region into classification items including at least one of protrusion, flatness, depression, and marginal protrusion based on the visual point information and luminance gradient information of the lesion region. In addition, the partial structure setting unit 113 includes a degree-of-importance setting unit 113a that sets a degree of importance that takes a large value for a region within the partial structure.

The diagnosis target image extraction unit 130A includes an extraction index evaluation value calculation unit 131A that calculates an extraction index evaluation value for extraction based on the information generated by the lesion information generation unit 110A, and the degree-of-clarity feature data.

In addition, the extraction index evaluation value calculation unit 131A includes a degree-of-clarity evaluation value calculation unit 131b that calculates an evaluation value that takes a superior value as the degree of clarity is higher from the degree-of-clarity feature data, and a degree-of-importance evaluation value calculation unit 131c that calculates an evaluation value that takes a superior value at a specific partial structure from the partial structure and the degree of importance.

Figure 8:
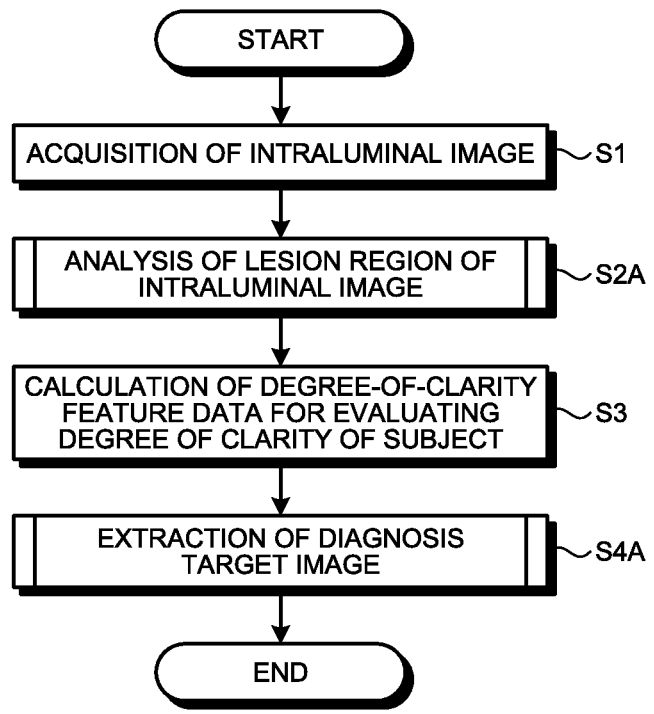
FIG. 8 is a flowchart illustrating image processing that is performed by the image processing device according to the second embodiment.

Next, an operation of the image processing device 1A will be described. FIG. 8 is a flowchart illustrating image processing that is performed by the image processing device according to the second embodiment. First, in Step S1, the image processing device 1A acquires an intraluminal image through the image acquisition unit 20 in the same manner as in the first embodiment.

Figure 9:
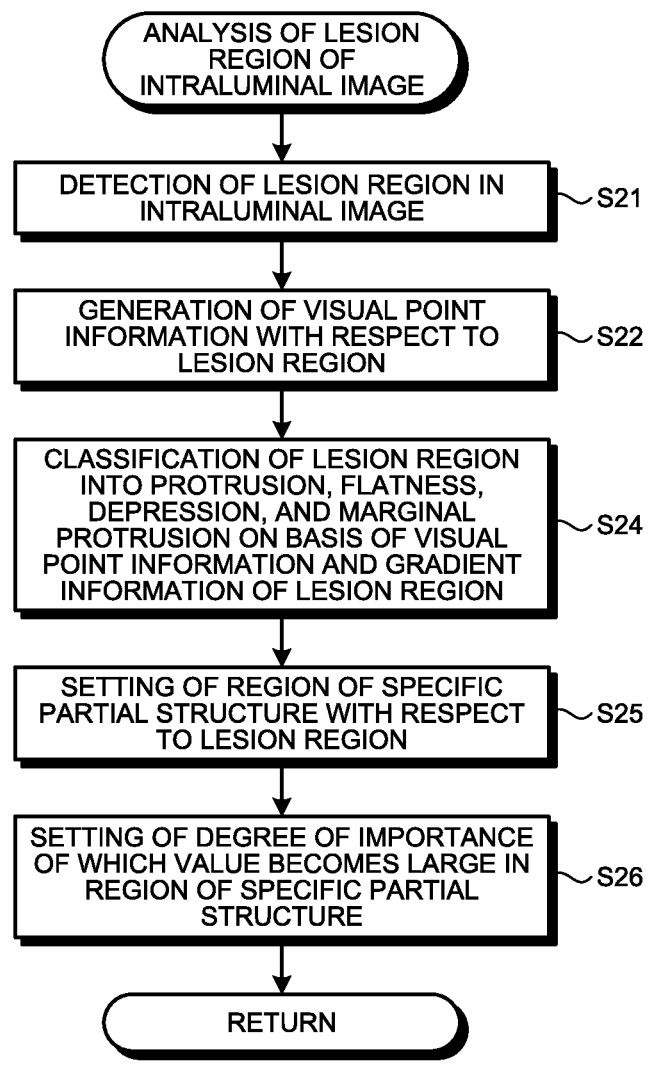
FIG. 9 is a flowchart illustrating lesion region analysis processing that is executed by the lesion information generation unit.

In subsequent Step S2A, the calculation unit 100A receives the intraluminal image, and analyzes a lesion region based on the intraluminal image. FIG. 9 is a flowchart illustrating lesion region analysis processing that is executed by the lesion information generation unit 110A.

In Step S21, the lesion region detection unit 111 detects a lesion region in the intraluminal image. As described above, the lesion region detection unit 111 detects the lesion region by using shape feature data.

In subsequent Step S22, the visual point estimation unit 112a generates visual point information for estimating a visual point with respect to the lesion region. As described above, the visual point estimation unit 112a calculates at least one determination value including a specific visual point among determination values for determining an upward visual point, a lateral visual point, and an inclined visual point, and sets the calculated determination value as visual point information.

In subsequent Step S24, the structure type classification unit 112b classifies the lesion region into classification items including at least one in the group consisting of protrusion, flatness, depression, and marginal protrusion based on the visual point information and the luminance gradient information of the lesion region.

Here, as an example of classification of a structure type, for every visual point that is obtained based on visual point information, the structure type classification unit 112b applies processing according to a configuration in which shape feature data and an identification device by machine learning are combined, and feature data with high shape description capability according to CoHOG (citation literature: "Co-occurrence Histograms of Oriented Gradients for Human Detection", TOSHIBA CORPORATION, 2010), in which a gradient vector direction in the lesion region is set as feature data, is classified by an identification device such as a support vector machine (SVM) that performs pattern recognition. Furthermore, there is no limitation to the CoHOG feature data as long as the feature data is the feature data with high shape description capability. In addition, the machine learning is also not limited to the SVM.

In subsequent Step S25, the partial structure setting unit 113 sets a region of a specific partial structure in the lesion region. The partial structure setting unit 113 sets the region of the specific partial structure based on a classification result by the structure type classification unit 112b. For example, the specific partial structure is any of a partial structure corresponding to a protrusion top portion, a partial structure corresponding to a surface center, a partial structure corresponding to a depression center, a partial structure corresponding to a rising portion, and a partial structure corresponding to a marginal protruding portion. The protrusion top portion is applied to total classification and corresponds to a top portion of a lesion. The rising portion is applied to a protrusion. The marginal protruding portion is applied to a marginal protrusion. A model shape of a lesion with respect to each visual point, and region information of the protrusion top portion, the rising portion, and the marginal protruding portion with respect to the model shape are provided in advance, and thus the structure type classification unit 112b performs alignment of a model shape in conformity to a visual point based on the visual point information and the luminance gradient information of the lesion region, and sets a region that overlaps the region information of the model shape subjected to the alignment as a region of a partial structure. Furthermore, as a value that is applied to calculate an evaluation value related to the partial structure, "1" is applied to the partial region, and "0" is applied to a site other than the partial region. For example, a specific partial structure is set by a user through the input unit 30.

In subsequent Step S26, the degree-of-importance setting unit 113a sets the degree of importance that takes a large value for the region of the specific partial structure. With regard to the region of the partial structure, the degree-of-importance setting unit 113a sets the degree of importance for a region within the partial structure to "1", and sets the degree of importance for a region outside the partial structure to "0" or a value of 0.0 to 1.0 that is linearly or non-linearly given in correspondence with distance information. In a case where the degree of importance of the site other than the region of the partial structure is set to the value of 0.0 to 1.0, with respect to the site other than the region of the partial structure, the degree-of-importance setting unit 113a sets the degree of importance to approach 1.0 as it is closer to the region of the partial structure. The degree-of-importance setting unit 113a may set the degree of importance only with respect to a set specific partial structure, or may set the degree of importance with respect to all partial structures. Then, the operation of the calculation unit 100A returns to the main routine.

In Step S3 subsequent to Step S2A, with respect to each of a plurality of regions which are set in the intraluminal image, the degree-of-clarity feature data calculation unit 120 calculates the degree of clarity of a subject as degree-of-clarity data in the same manner as in the first embodiment.

Figure 10:
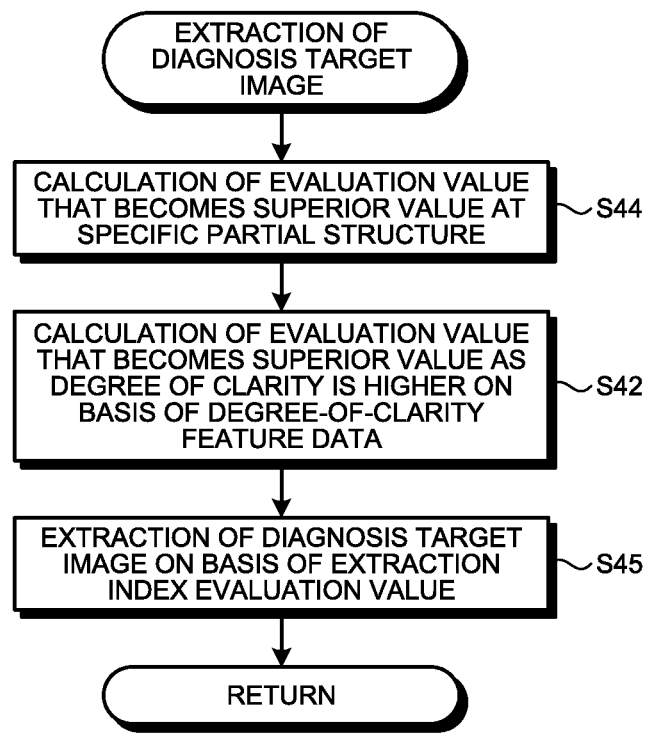
FIG. 10 is a flowchart illustrating diagnosis target image extraction processing that is executed by the diagnosis target image extraction unit.

In Step S4A subsequent to Step S3, the diagnosis target image extraction unit 130A calculates the extraction index evaluation value, and makes a determination by using the calculated extraction index evaluation value, and the threshold value that is set in advance to extract the diagnosis target image. FIG. 10 is a flowchart illustrating diagnosis target image extraction processing that is executed by the diagnosis target image extraction unit 130A.

In Step S44, the degree-of-importance evaluation value calculation unit 131c calculates an evaluation value that takes a superior value at a specific partial structure based on the partial structure and the degree of importance, and sets the evaluation value as the extraction index evaluation value. The degree-of-importance evaluation value calculation unit 131c calculates the evaluation value by adding an application value that is applied to the partial structure in the lesion region, and the degree of importance, and applies the evaluation value that takes a superior value at a specific partial structure with respect to the intraluminal image including the lesion region including the partial structure that is set as the specific partial structure. According to this, in the second embodiment, description will be given on the assumption that the evaluation value is applied to only an intraluminal image including a specific partial structure that is set. The evaluation value calculated by the degree-of-importance evaluation value calculation unit 131c is an extraction index evaluation value related to the degree of importance of the partial structure, and the value becomes larger as a region occupied by the specific partial structure in the lesion region is larger. Furthermore, an evaluation value of an intraluminal image that does not include the set specific partial structure may be set to 0. In addition, in a case where a plurality of the specific partial structures are set, an evaluation value in which the degree of importance is applied to each partial structure is calculated.

Here, in a case where the plurality of partial structures are set, evaluation values which are calculated for the plurality of partial structures are added in calculation. In this case, the maximum value of the evaluation values which can be obtained is normalized to "1", and a value after the normalization may be set as the evaluation value.

In Step S42 subsequent to Step S44, with respect to the evaluation value that is obtained in Step S3, the degree-of-clarity evaluation value calculation unit 131b calculates an evaluation value that takes a superior value as the degree of clarity is higher in the same manner as in the first embodiment, and sets the evaluation value as the extraction index evaluation value.

In Step S45 subsequent to Step S42, the diagnosis target image extraction unit 130A makes a determination by using the extracted index evaluation values acquired in Steps S44 and S42 and a threshold value that is set in advance to extract the diagnosis target image. The diagnosis target image extraction unit 130A extracts an intraluminal image, in which the evaluation value related to the partial structure and the evaluation value related to the degree of clarity exceed threshold values which are set in advance with respect to the respective evaluation values, as the diagnosis target image.

Then, the calculation unit 100A outputs the extraction result in Step S4A. In correspondence with this, the control unit 10 causes the display unit 40 to display a region that is determined as an abnormal region. In addition, the extraction result in Step S4A may be recorded in the recording unit 50. Then, the operation of the image processing device 1A is completed.

As described above, according to the second embodiment, since the structure type is classified based on the visual point information indicating a visual point with respect to a lesion in the intraluminal image and the luminance gradient information, and the diagnosis target image is extracted based on the evaluation value calculated based on the partial region that is set in correspondence with the structure type, and the evaluation value of the degree of clarity that is calculated from the degree-of-clarity feature data, it is possible to extract a diagnosis target image that is used in diagnosis and is suitable for the diagnosis. According to this, it is possible to extract an intraluminal image that is suitable for rear-stage processing or an object of observation.

Furthermore, in the second embodiment, description has been given of a case where the degree-of-importance setting unit 113a sets the degree of importance with respect to the partial structure, but setting of the degree of importance may not be performed. In this case, the partial structure setting unit 113 has a configuration that is not provided with the degree-of-importance setting unit 113a, and the degree-of-importance evaluation value calculation unit 131c calculates an evaluation value in which the degree of importance is not applied to the partial structure.

Third Embodiment

Figure 11:
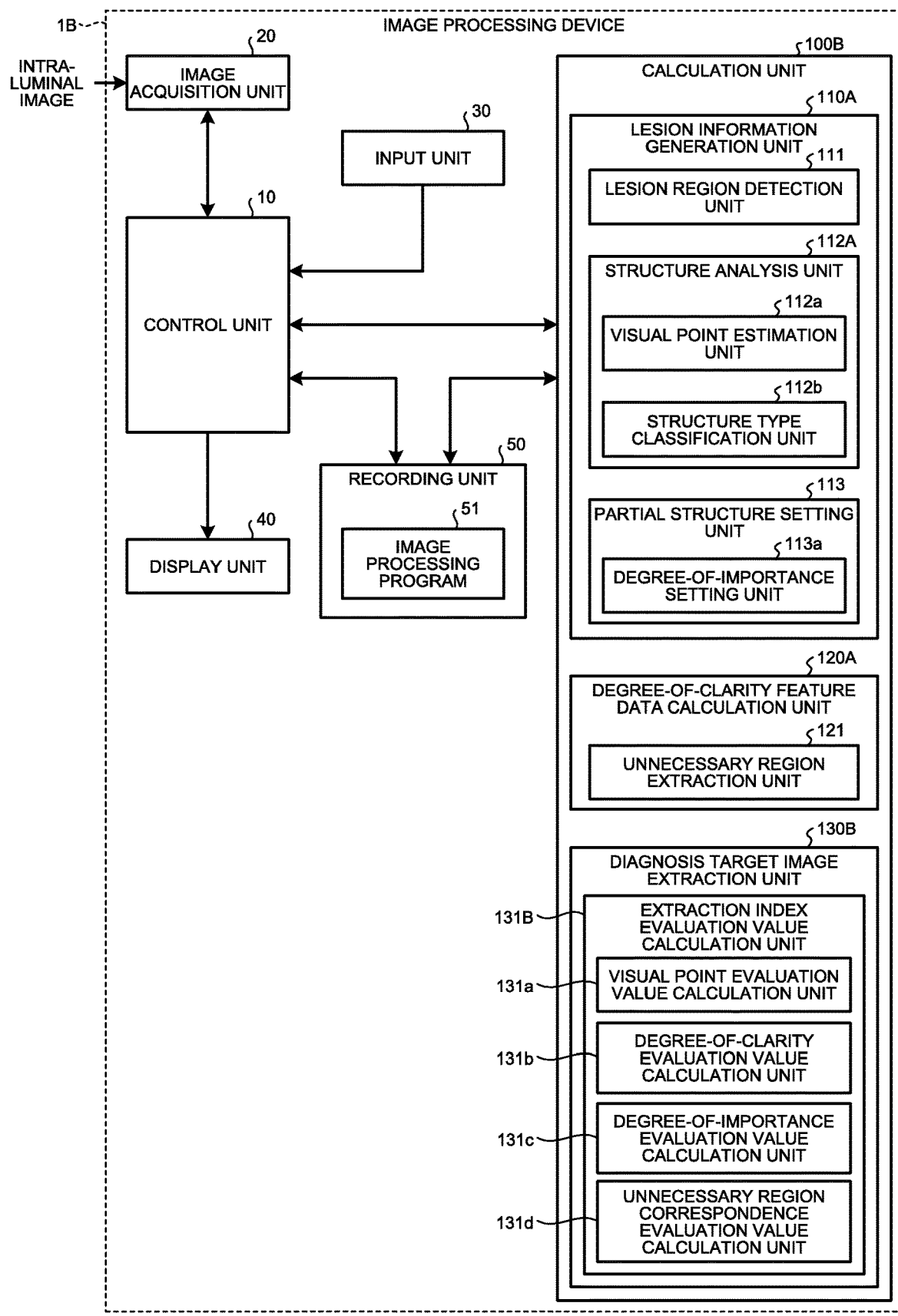
FIG. 11 is a block diagram illustrating a functional configuration of an image processing device according to a third embodiment.

FIG. 11 is a block diagram illustrating a functional configuration of an image processing device according to a third embodiment. In the following description, the same reference numerals will be given the same constituent portions as the constituent portions of the image processing devices 1 and 1A according to the first and second embodiments. An image processing device 1B illustrated in FIG. 11 includes a control unit 10 that controls an operation of the entirety of the image processing device 1B, an image acquisition unit 20 that acquires image data that is generated by capturing the inside of a lumen with an imaging device, an input unit 30 that inputs a signal corresponding to an operation from the outside to the control unit 10, a display unit 40 that performs display of various pieces of information and images, a recording unit 50 that stores image data acquired by the image acquisition unit 20 and various programs, and a calculation unit 100B that executes predetermined image processing with respect to the image data.

The calculation unit 100B includes a lesion information generation unit 110A, a degree-of-clarity feature data calculation unit 120A, and a diagnosis target image extraction unit 130B.

The degree-of-clarity feature data calculation unit 120A includes an unnecessary region extraction unit 121 that extracts coordinate information of an unnecessary region such as a non-mucosal region and a luminance-saturated region.

The diagnosis target image extraction unit 130B makes a determination by using an extraction index evaluation value and a threshold value that is set in advance to extract a diagnosis target image. The diagnosis target image extraction unit 130B includes an extraction index evaluation value calculation unit 131B that calculates the extraction index evaluation value for extraction based on a partial region and degree-of-clarity feature data.

The extraction index evaluation value calculation unit 131B includes a visual point evaluation value calculation unit 131a that calculates an evaluation value that takes a superior value at a specific visual point, a degree-of-clarity evaluation value calculation unit 131b that calculates an evaluation value that takes a superior value as the degree of clarity is higher from the degree-of-clarity feature data, a degree-of-importance evaluation value calculation unit 131c that calculates an evaluation value that takes a superior value at a specific partial structure from the degree of importance, and an unnecessary region correspondence evaluation value calculation unit 131d that calculates an evaluation value in correspondence with an unnecessary region.

Figure 12:
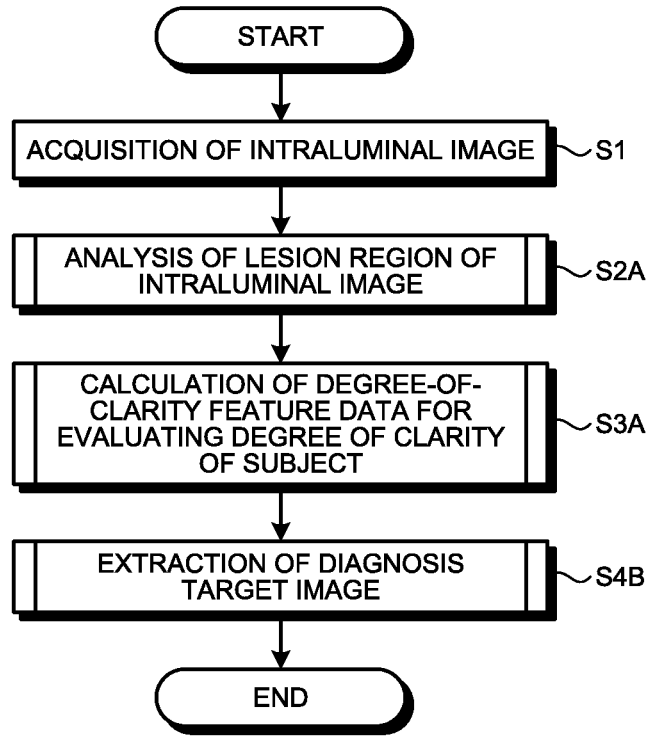
FIG. 12 is a flowchart illustrating image processing that is performed by the image processing device according to the third embodiment.

Next, an operation of the image processing device 1B will be described. FIG. 12 is a flowchart illustrating image processing that is performed by the image processing device according to the third embodiment. First, in Step S1, the image processing device 1B acquires an intraluminal image through the image acquisition unit 20 in the same manner as in the first embodiment.

In subsequent Step S2A, the calculation unit 100B receives the intraluminal image, and analyzes a lesion region based on the intraluminal image. In Step S2A, processing is executed in accordance with the flowchart illustrated in FIG. 9.

Figure 13:
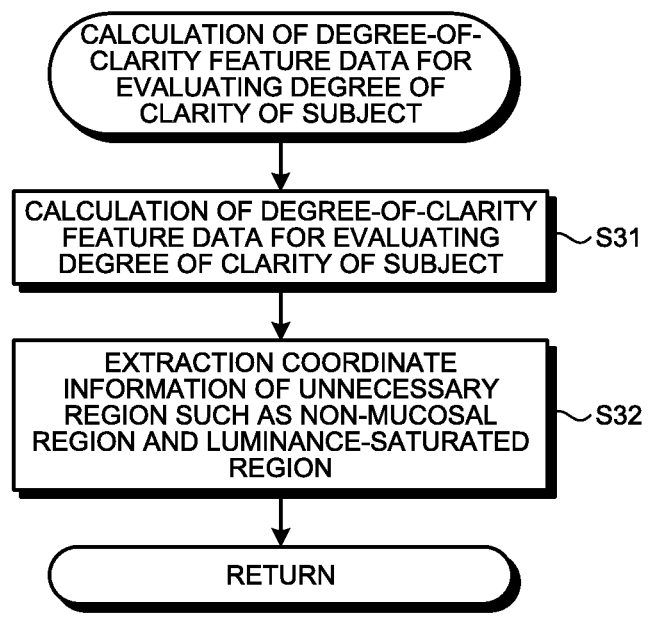
FIG. 13 is a flowchart illustrating degree-of-clarity feature data calculation processing that is executed by a degree-of-clarity feature data calculation unit.

In Step S3A subsequent to Step S2A, with respect to each of a plurality of regions which are set in the intraluminal image, the degree-of-clarity feature data calculation unit 120A calculates the degree of clarity of a subject as degree-of-clarity feature data. FIG. 13 is a flowchart illustrating degree-of-clarity feature data calculation processing that is executed by the degree-of-clarity feature data calculation unit 120A.

In Step S31, with respect to each of the plurality of regions which are set in the intraluminal image, the degree-of-clarity feature data calculation unit 120A calculates the degree of clarity of a subject as degree-of-clarity feature data.

In Step S32, the unnecessary region extraction unit 121 extracts coordinate information of an unnecessary region such as a non-mucosal region and a luminance-saturated region. Examples of the unnecessary region include a residue of which color information is relatively different from a mucosal color, a blood region, a bubble region showing a high frequency component, a specular reflection region showing low-chroma and high-luminance information, a luminance-saturated region showing high-luminance information, and the like. These regions are detected based on a relative position relationship with respect to a color distribution of a mucosal region on a color feature data space by using a different in color information. Specifically, a G/R value is calculated with respect to each pixel in the intraluminal image, a region in which the G/R value is equal to or less than a determination threshold value for determining the mucosal region, that is, a reddish region is set as a detection target region. In addition, with regard to the bubble region, a high-frequency component in a convex direction is set as the bubble region. For example, as disclosed in JP 2007-313119 A, the unnecessary region extraction unit 121 detects the bubble region by performing matching a bubble model that is set based on the feature of a bubble image such as a contour portion of a bubble and an arc-shaped convex edge due to illumination reflection at the inside of the bubble, and an edge that is extracted from the intraluminal image. In addition, the specular reflection region and the luminance-saturated region are detected by comparing a region in which a red color component is equal to or greater than a predetermined threshold value, or a luminance value is equal to or greater than a predetermined value and a chroma is equal to or less than a predetermined value, and a threshold value that is determined in advance. Furthermore, with regard to the coordinate information generated by the unnecessary region extraction unit 121, for example, a region determined as an unnecessary region is set to "255", and a region that is not determined as the unnecessary region is set to "0", thereby constructing a mask image correlated with any one of the values, and coordinates attached to a pixel. After extraction of coordinate information of the unnecessary region, the operation of the calculation unit 100B returns to the main routine.

In Step S4B subsequent to Step S3A, the diagnosis target image extraction unit 130B makes a determination by using the extraction index evaluation value and a threshold value that is set in advance to extract the diagnosis target image. FIG. 14 is a flowchart illustrating diagnosis target image extraction processing that is executed by the diagnosis target image extraction unit 130B.

In Step S41, with respect to the evaluation value obtained in Step S2A, the visual point evaluation value calculation unit 131a calculates an evaluation value that takes a superior value at a specific visual point, and sets the evaluation value as the extraction index evaluation value.

In Step S44 subsequent to Step S41, the degree-of-importance evaluation value calculation unit 131c calculates an evaluation value that takes a superior value at a specific partial structure from the degree of importance, and sets the evaluation value as the extraction index evaluation value.

In Step S42 subsequent to Step S44, with respect to the evaluation value that is obtained in Step S3A, the degree-of-clarity evaluation value calculation unit 131b calculates an evaluation value that takes a superior value as the degree of clarity is higher as in the same manner as in the first embodiment, and sets the evaluation value as the extraction index evaluation value.

In Step S46 subsequent to Step S42, with respect to the evaluation value that is calculated by the degree-of-clarity evaluation value calculation unit 131b, the unnecessary region correspondence evaluation value calculation unit 131d performs evaluation value subtraction in correspondence with the unnecessary region, and sets the calculated evaluation value as the extraction index evaluation value. Specifically, the unnecessary region correspondence evaluation value calculation unit 131*d* performs subtraction processing of the evaluation value calculated by the degree-of-clarity feature data calculation unit 120A in correspondence with arrangement of unnecessary regions by using a subtraction value that is set to be a higher subtraction value with respect to the evaluation value as a position of the unnecessary region is closer to a region in which the degree of importance is higher. For example, the unnecessary region correspondence evaluation value calculation unit 131*d* performs the subtraction processing of the evaluation value by using a subtraction value that approaches 0.2 as it is closer to a region in which the degree of importance is high, and that approaches 0.0 as it is further spaced away from the region in which the degree of importance is high. The unnecessary region correspondence evaluation value calculation unit 131*d* sets the evaluation value after subtraction as the extraction index evaluation value.

In Step S47 subsequent to Step S46, the diagnosis target image extraction unit 130B makes a determination by using the extraction index evaluation values acquired in Steps S41, S44, S42, and S46 and a threshold value that is set in advance to extract the diagnosis target image. The diagnosis target image extraction unit 130B extracts an intraluminal image, in which each of the evaluation value related to the visual point information, the evaluation value related to the partial structure, the evaluation value related to the degree of clarity, and the evaluation value related to the unnecessary region exceeds the threshold value, as the diagnosis target image. Furthermore, the evaluation value calculated by the unnecessary region correspondence evaluation value calculation unit 131*d* includes an evaluation value in a unit of a detected lesion. The diagnosis target image extraction unit 130B makes a determination by comparing the evaluation value that is calculated by the unnecessary region correspondence evaluation value calculation unit 131*d* and a threshold value that is set in advance in correspondence with an area of a lesion region detected in the lesion detection.

Then, the calculation unit 100 outputs the extraction result in Step S4B. According to this, the control unit 10 causes the display unit 40 to display a region that is determined as an abnormal region. In addition, the extraction result in Step S4B may be recorded in the recording unit 50. Then, the operation of the image processing device 1B is terminated.

As described above, according to the third embodiment, since the structure type is classified based on the visual point information indicating a visual point with respect to a lesion in the intraluminal image, and the diagnosis target image is extracted based on the evaluation value calculated based on the partial region that is set in correspondence with a partial structure of the structure type, the evaluation value related to the visual point information, the evaluation value of the degree of clarity that is calculated from the degree-of-clarity feature data, and the evaluation value related to the unnecessary region in the intraluminal image, it is possible to extract a diagnosis target image that is suitable for a diagnosis target. According to this, it is possible to extract an intraluminal image that is suitable for rear-stage processing or an object of observation.

Furthermore, in the third embodiment, description has been given of a case where the degree-of-importance setting unit 113*a* sets the degree of importance with respect to the partial structure, but setting of the degree of importance may not be performed as in the second embodiment. In this case, the partial structure setting unit 113 has a configuration that is not provided with the degree-of-importance setting unit 113*a*, and the degree-of-importance evaluation value calculation unit 131*c* calculates an evaluation value in which the degree of importance is not applied to the partial structure.

In addition, in the third embodiment, description has been given of a case where the unnecessary region correspondence evaluation value calculation unit 131*d* performs recalculation of the evaluation value with respect to the evaluation value calculated by the degree-of-clarity feature data calculation unit 120A, but application is also possible to the evaluation value related to the visual point information or the evaluation value related to the partial structure. In addition, an extraction index evaluation value of which an evaluation value is recalculated in correspondence with the unnecessary region may not be used in extraction processing of the intraluminal image.

Other Embodiments

Hereinbefore, embodiments for carrying out the disclosure have been described, but the disclosure is not limited only to the first to third embodiments. For example, the degree of circularity may be calculated as the feature data instead of the degree-of-clarity feature data, and the extraction evaluation value may be calculated from the degree of circularity and the visual point information. As described above, the disclosure can include various embodiments and the like which are not described here.

INDUSTRIAL APPLICABILITY

As described above, the image processing device, the operation method of the image processing device, and the operation program of the image processing device according to the disclosure are useful to extract an intraluminal image suitable for diagnosis from an intraluminal image group.

According to the disclosure, it is possible to extract an intraluminal image suitable for diagnosis from an intraluminal image group.

Additional advantages and modifications will readily occur to those skilled in the art. Therefore, the disclosure in its broader aspects is not limited to the specific details and representative embodiment shown and described herein. Accordingly, various modifications may be made without departing from the spirit or scope of the general inventive concept as defined by the appended claims and their equivalents.

What is claimed is:

1. An image processing device comprising
a processor comprising hardware, wherein the processor is configured to execute:
    acquiring intraluminal images;
    generating, for each of the intraluminal images, lesion information by estimating a visual point with respect to a lesion region extracted from each of the intraluminal images and analyzing a three-dimensional structure of the lesion, the lesion information indicating any of a top portion, a rising portion, and a marginal protruding portion in the lesion region; and
    extracting, based on the lesion information, a target image satisfying a prescribed condition from the intraluminal images.

2. The image processing device according to claim 1, wherein the processor is configured to execute generating the visual point information by using at least one among transition information of contour edge intensity of the lesion region, luminance information of the lesion region, and gradient information of the periphery of the lesion region.

3. The image processing device according to claim 2, wherein the processor is configured to execute setting a region of a specific partial structure with respect to the lesion region.

4. The image processing device according to claim 3, wherein the specific partial structure is at least one selected from the group consisting of a protrusion top portion, a surface center, a depression center, a protrusion rising portion, and a marginal protruding portion.

5. The image processing device according to claim 3, wherein the processor is configured to execute setting a degree of importance that takes a greater value for a region within the specific partial structure as compared with a value for a region outside the specific partial structure.

6. The image processing device according to claim 2, wherein the processor is configured to execute classifying the legion region into classification items selected from a partial structure group consisting of protrusion, flatness, depression, and marginal protrusion based on the visual point information and the luminance information of the lesion region.

7. The image processing device according to claim 1, the processor is configured to execute calculating degree-of-clarity feature data indicating the degree of clarity of each of the intraluminal image.

8. The image processing device according to claim 7, wherein the degree-of-clarity feature data is at least one selected from the group consisting of a color drift amount, the degree of blur, a noise amount, a luminance-saturated area ratio, contrast information, frequency information, and edge information.

9. The image processing device according to claim 7, wherein the processor is configured to execute extracting coordinate information of an unnecessary region from each of the intraluminal images.

10. The image processing device according to claim 7, wherein the processor is configured to execute calculating an evaluation value for extraction based on the lesion information and the degree-of-clarity feature data.

11. The image processing device according to claim 10, wherein the processor is configured to execute calculating an evaluation value that takes a superior value at a specific visual point.

12. The image processing device according to claim 11, wherein the processor is configured to execute calculating an evaluation value for evaluating at least one visual point among an upward visual point, a lateral visual point, and an inclined upward visual point.

13. The image processing device according to claim 11, wherein the processor is configured to execute calculating at least one evaluation value among a plurality of evaluation values which respectively evaluate an upward visual point, a lateral visual point, and an inclined upward visual point.

14. The image processing device according to claim 10, wherein the processor is configured to execute calculating an evaluation value that takes a superior value at a specific partial structure based on the degree of importance that is set in correspondence with a distance to the partial structure.

15. The image processing device according to claim 14, wherein
the specific partial structure includes at least one selected from the group consisting of a protrusion top portion, a surface center, a depression center, a protrusion rising portion, and a marginal protruding portion, and
the processor is configured to execute the calculating the evaluation value in correspondence with a structure that constructs the specific partial structure.

16. The image processing device according to claim 14, wherein the specific partial structure a plurality of structures selected from the group consisting of a protrusion top portion, a surface center, a depression center, a protrusion rising portion, and a marginal protruding portion, and
the processor is configured to execute the calculating the evaluation value with respect to each of the structures which constitute the specific partial structure.

17. The image processing device according to claim 10, wherein the processor is configured to execute calculating an evaluation value that takes a superior value at a high degree of clarity based on the degree-of-clarity feature data.

18. The image processing device according to claim 17, wherein the degree-of-clarity feature data is composed of at least one piece of feature data selected from a feature data group consisting of a color drift amount, the degree of blur, a noise amount, a luminance-saturated area ratio, contrast information, frequency information, and edge information, and
the processor is configured to execute the calculating the evaluation value of the degree of clarity corresponding to the feature data that constitutes the degree-of-clarity feature data.

19. The image processing device according to claim 17, wherein the degree-of-clarity feature data is composed of a plurality of pieces of feature data selected from a feature data group consisting of a color drift amount, the degree of blur, a noise amount, a luminance-saturated area ratio, contrast information, frequency information, and edge information, and
the processor is configured to execute calculating an evaluation value of the degree of clarity with respect to each of the plurality of pieces of feature data which constitute the degree-of-clarity feature data.

20. The image processing device according to claim 7, wherein the processor is configured to execute calculating an evaluation value corresponding to an unnecessary region in each of the intraluminal image.

21. The image processing device according to claim 1, wherein the processor is configured to execute the extracting the target image by making a determination step by step on a plurality of evaluation values different from each other by using a threshold value, which is set in correspondence with each of the evaluation values.

22. The image processing device according to claim 1, wherein the processor is configured to execute the extracting the target image based on a distribution of evaluation values, which are constituted in a multi-dimensional evaluation value space, in a range that is set in advance.

23. The image processing device according to claim 1, wherein the processor is configured to execute ranking the intraluminal images having an evaluation value in a range that is set in advance, and sequentially extracting target images in a number set in advance from a higher side.

24. An operation method comprising:
acquiring intraluminal images;
generating, for each of the intraluminal images, lesion information by estimating a visual point with respect to a lesion region extracted from each of the intraluminal images and analyzing a three-dimensional structure of the lesion region, the lesion information indicating any of a top portion, a rising portion, and a marginal protruding portion in the lesion region; and
extracting, based on the lesion information, a target image satisfying a prescribed condition from the intraluminal images.

25. A non-transitory computer-readable recording medium on which an executable program is recorded, the program instructing a processor of an image processing device to execute:
acquiring intraluminal images;
generating, for each of the intraluminal images, lesion information by estimating a visual point with respect to a lesion region extracted from each of the intraluminal images and analyzing a three-dimensional structure of the lesion region, the lesion information indicating any of a top portion, a rising portion, and a marginal protruding portion in the lesion region; and
extracting, based on the lesion information, a target image satisfying a prescribed condition from the intraluminal images.

* * * * *